United States Patent [19]

Ouziel

[11] Patent Number: 5,457,233
[45] Date of Patent: Oct. 10, 1995

[54] PROCESS FOR THE PREPARATION OF AMINES

[75] Inventor: Philippe Ouziel, Altkirch, France

[73] Assignee: Ciba-Geigy Corporation, Ardsley, N.Y.

[21] Appl. No.: 345,274

[22] Filed: Nov. 28, 1994

Related U.S. Application Data

[63] Continuation of Ser. No. 117,848, Sep. 7, 1993, abandoned.

[30] Foreign Application Priority Data

Sep. 11, 1992 [CH] Switzerland ............ 02866/92

[51] Int. Cl.$^6$ .................................................. C07C 209/28
[52] U.S. Cl. .................................... 564/473; 564/471
[58] Field of Search ........................... 564/473, 471

[56] References Cited

U.S. PATENT DOCUMENTS

| | | | |
|---|---|---|---|
| 2,179,215 | 11/1939 | Jacobson | 564/471 |
| 2,366,534 | 1/1945 | Kirby | 260/583 |
| 4,210,605 | 7/1980 | Hoshino et al. | 260/585 B |
| 4,405,811 | 9/1983 | Stagryn et al. | 564/471 |
| 4,683,336 | 7/1987 | Blackhurst | 564/480 |

FOREIGN PATENT DOCUMENTS

| | | |
|---|---|---|
| 1227450 | 10/1966 | Germany . |
| 0887563 | 12/1981 | U.S.S.R. . |
| 1055616 | 1/1967 | United Kingdom . |

OTHER PUBLICATIONS

Chemical Abstracts, vol. 66, 2184q (1967).
Derwent Abstract, 87 393 (SU 887,563) (1981).

*Primary Examiner*—Glennon H. Hollrah
*Assistant Examiner*—Scott C. Rand
*Attorney, Agent, or Firm*—Kevin T. Mansfield

[57] ABSTRACT

A process for the preparation of amines of formula

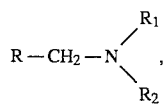 (1)

wherein the variables are defined as in the claims, which comprises reacting 1 molar equivalent of an amine of formula

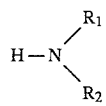 (2)

with 0.8 to 1.5 molar equivalents of an aldehyde of formula

R—CHO  (3)

and 0.8 to 2 molar equivalents of formic acid, in aqueous medium, and adjusting the pH by addition of a mineral acid such that, at the conclusion of the reaction, the pH is in the range from 3 to 7. The compounds obtainable by the process are useful intermediates for the synthesis of dyeing assistants.

9 Claims, No Drawings

PROCESS FOR THE PREPARATION OF AMINES

This application is a continuation, of application Ser. No. 08/117,848, filed Sep. 7, 1993, now abandoned.

The present invention relates to a process for the preparation of tertiary amines.

It has already been disclosed in SU 887 563 to prepare tertiary amines by reductive amination of primary or secondary amines with formaldehyde and formic acid. In this process, the amine is first treated with hydrochloric acid and then reacted with stoichiometric amounts of formic acid and formaldehyde, the pH remaining strongly acid during the course of the entire reaction. The product is obtained in a maximum yield of 80%. In this process, the temperatures are high and the reaction times long.

It is also known to prepare tertiary amines such as N-methyl-N,N-diallylamine by the Eschweiler-Clarke reaction in which a secondary amine, an aldehyde and excess formic acid are reacted with one another. This reaction, which gives a good yield, has a poor ecological balance, in particular a high TOC, as the mother liquor contains large amounts of formic acid salts.

Surprisingly, it has now been found that the corresponding reaction is able to proceed rapidly at low temperature, in good yield and in good ecological balance by using the reactants in about stoichiometric amounts or solely in low excess, and controlling the pH of the reaction by adding a mineral acid such that, at the conclusion of the reaction, the pH of the reaction mixture is in the neutral to slightly acid range.

Accordingly, the invention relates to a process for the preparation of amines of formula

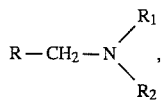  (1)

wherein R is hydrogen or a linear or branched aliphatic radical, and $R_1$ and $R_2$ are each independently of the other a saturated or unsaturated aliphatic radical, which comprises reacting 1 molar equivalent of an amine of formula

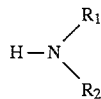  (2)

with 0.8 to 1.5 molar equivalents of an aldehyde of formula

  (3)

and 0.8 to 2 molar equivalents of formic acid, in aqueous medium, and adjusting the pH by addition of a mineral acid such that, at the conclusion of the reaction, the pH is in the range from 3 to 7, and wherein R, $R_1$ and $R_2$ in formulae (2) and (3) are each as defined above.

An aliphatic radical R is typically a $C_1$-$C_6$alkyl radical. Illustrative examples are methyl, ethyl, n- or isopropyl, n-, iso-, sec- or tert-butyl or straight-chain or branched pentyl or hexyl. An aliphatic radical R is preferably $C_1$-$C_4$alkyl and is most preferably methyl or ethyl.

R is preferably methyl, ethyl or, most preferably, hydrogen. $R_1$ and/or $R_2$ as a saturated aliphatic radical may independently have the same meanings as those given in connection with R.

$R_1$ and $R_2$ as an unsaturated aliphatic radical are each independently of the other a $C_3$-$C_8$alkenyl radical, typically allyl, 1-propenyl, isopropenyl, 2- or 3-methylallyl, 3-butenyl or 3,3-dimethylallyl.

$R_1$ and $R_2$ may be different or, preferably, identical, and are each most preferably an unsaturated aliphatic radical. It is especially preferred that $R_1$ and $R_2$ are each allyl.

A preferred embodiment of this invention relates to the preparation of N-methyl-N,N-diallylamine from diallylamine and formaldehyde.

The choice of mineral acid in the process is not crucial. All customary acids may suitably be used, typically sulfuric acid, hydrochloric acid, nitric acid or phosphoric acid. The preferred mineral acid is hydrochloric acid or sulfuric acid.

The amine of formula (2), the aldehyde of formula (3) and the formic acid are preferably used in a molar ratio of 1/1/1.

The process is conveniently carded out under normal pressure and at elevated temperature, i.e. in the temperature range from 40° to 100° C. and preferably from 60° to 80° C. One variant of the process consists in carrying out the process under excess pressure, i.e. typically under a pressure of up to 5 atoms and at temperatures above 100° C.

It is preferred to carry out the reaction such that the pH of the reaction mixture at the conclusion of the reaction is 4–6. The amount of acid required is c. 0.3 to 2.0 molar equivalents and, preferably, 0.5 to 1 molar equivalent, of mineral acid per molar equivalent of amine of formula (2).

A particularly preferred embodiment of the invention relates to a process for the preparation of N-methyl-N,N-diallylamine, which comprises reacting 1 molar equivalent of N,N-diallylamine with 1 molar equivalent of (para)formaldehyde and 1 molar equivalent of formic acid in aqueous medium and adjusting the pH by addition of 0.5 to 1 molar equivalent of hydrochloric acid or sulfuric acid such that, upon completion of the reaction, the pH is 4–6.

The procedure comprises charging the aldehyde of formula (3) and the formic acid to the reactor in the presence of water and heating the reaction solution to the desired reaction temperature. The amine of formula (2) is then added dropwise, whereupon the pH of the reaction mixture rises slowly and is kept in the range from 3–7, preferably from 4–6, until completion of the reaction by addition of mineral acid. It is preferred to adjust the pH to a specific value within the claimed range by adding the amine and keeping this value until completion of the reaction by addition of mineral acid.

A variant of the process comprises charging the aldehyde of formula (3), the formic acid and sulfuric acid ($H_2SO_4$) or phosphoric acid to the reactor and adding the amine of formula (2) dropwise gradually. The reaction then commences at a strongly acid pH, which rises slowly in the course of the reaction and, upon conclusion of the reaction, reaches a value within the claimed range.

It is further possible to charge the amine of formula (2) and the formic acid to the reactor in the presence of water and to add the aldehyde of formula(3) dropwise. In this case, the mineral acid can be added at the start of, or during, the reaction.

The reaction solution may contain further ingredients, conveniently antifoams or wetting agents and polymerisation inhibitors such as hydroquinone derivatives.

The reaction times vary depending on the reactants and the specific reaction conditions, but are normally from 30 minutes to 5 hours and, preferably, from 1 to 3 hours.

The reaction mixtures are worked up in per se known manner, conveneitnly by adjusting the pH to the alkaline range, separating the two phases that form and subjecting the organic phase containing the amine to distillation.

3

The compounds obtainable by the process of this invention are useful intermediates for, inter alia, the synthesis of dyeing assistants.

The invention is illustrated by the following Examples in which parts and percentages are by weight.

EXAMPLE 1

219.4 parts of 84% formic acid, 125.3 pans of 95.5% paraformaldehyde, 249 parts of water, 0.2 part of hydroquinone and 2 pans of an antifoam (2,4,7,9-tetramethyl-5-decyn-4,7-diol) are charged to a suitable reactor equipped with stirrer, thermometer, reflux condenser, a pH electrode and an inlet for the feed of hydrochloric acid, and the resultant suspension is heated to 65° C. Over the course of c. 45 minutes, 388.8 parts of diallyl amine are added dropwise at a temperature of c. 58°–62° C. During this addition, the pH rises slowly and when it has reached 5.5 is kept constant at this value with 37% hydrochloric acid. When the addition of diallyl amine is complete, the reaction is heated to 65°–70° C. and stirred for c. 2 hours at this temperature and pH 5.5.

The reaction mixture is cooled to room temperature and adjusted to pH>12. The two phases that form are separated. The organic phase is stabilised with 0.1 part of hydroquinone, the water contained therein is removed as an azeotrope by distillation and N-methyl-N,N-diallylamine distills. Boiling point 112°–115° C.; yield 406 parts (91.4%) of product in 99.8% purity. The mother liquor has a TOC of ≦8000 ppm.

EXAMPLE 2

215.3 parts of 85% formic acid, 125.5 parts of 95.5% paraformaldehyde, 290 parts of water, 204.3 parts of 96% $H_2SO_4$ and 0.2 part of hydroquinone are charged to the apparatus of Example 1 and the resultant suspension is heated to 75° C. Then 388.8 parts of diallyl amine are added dropwise over c. 30 minutes, while keeping the temperature at 70°–70° C. When the addition of diallyl amine is complete, the reaction mixture is stirred for 3 hours at 75° C. and the product is isolated as described in Example 1. Yield: 408 parts (91.9%) of N-methyl-N,N-diallylamine in 99.7% purity. The mother liquor has a TOC of ≦9800 ppm.

Comparative Example

An experiment is carded out using the Eschweiler-Clarke process. The reaction conditions and results are summarised in the table and compared with those of Examples 1 and 2. The table also contains the data of SU 887 563, Example 4.

| Process | Eschweiler Clarke | SU 887 563 Example 4 | Example 1 | Example 2 |
|---|---|---|---|---|
| diallyl aminie (mol) | 1 | 1 | 1 | 1 |
| (para)formaldehyde (mol) | 1.2 | 1 | 1 | 1 |
| formic acid (mol) | 2.4 | 1 | 1 | 1 |
| HCl or $H_2SO_4$ (mol) | — | 1 | 0.9 | 0.5 |
| reaction temp. (°C.) | 80 | 100 | 65 | 75 |
| reaction time (h) | 3 | 9 | 2 | 3 |
| final pH | 3.9 | —[1)] | 5.5 | 4.5 |
| TOC of mother liquor (ppm) | ≧60000 | — | 8000 | 9800 |
| yield (% theory) | 90–92 | 78 | 91.4 | 91.9 |

[1)]not indicated: substantially less than 3 according to our findings when the Example is reproduced

What is claimed is:

1. A process for the preparation of an amine of the formula

(1)

wherein R is hydrogen or a linear or branched aliphatic radical, and $R_1$ and $R_2$ are each independently of the other a saturated or unsaturated aliphatic radical, which comprises A) charging 0.8 to 1.5 molar equivalents of an aldehyde of the formula

R—CHO        (3), wherein R is as defined above, and formic acid to a reactor in the presence of water, heating the reaction solution to a temperature of 40° to 100° C., and adding 1 molar equivalent of an amine of the formula

(2)

wherein $R_1$ and $R_2$ are as defined above, while keeping the pH of the reaction mixture in the range of from 4–6 by addition of mineral acid until completion of the reaction; or B) charging 1 molar equivalent of an amine of the formula

(2)

wherein $R_1$ and $R_2$ are as defined above, and formic acid to a reactor in the presence of water, heating the reaction solution to a temperature of 40° to 100° C., and adding 0.8 to 1.5 molar equivalents of an aldehyde of the formula

R—CHO (3), wherein R is as defined above, while keeping the pH of the reaction mixture in the range of from 4–6 by addition of mineral acid until completion of the reaction.

2. A process according to claim 1, wherein R is hydrogen, methyl or ethyl.

3. A process according to claim 1, wherein $R_1$ and $R_2$ are each independently of the other allyl, 1-propenyl, isopropenyl, 2- or 3-methylallyl, 3-butenyl or 3,3-dimethylallyl.

4. A process according to claim 1, wherein R is hydrogen and $R_1$ and $R_2$ are each allyl.

5. A process according to claim 1, wherein the mineral acid is hydrochloric acid or sulfuric acid.

6. A process according to claim 1, wherein the amine of formula (2), the aldehyde of formula (3) and the formic acid used in the molar ratio of 1/1/1.

7. A process according to claim 1, wherein 0.3 to 2.0 molar equivalents, of mineral acid is used per molar equivalent of amine of formula (2).

8. A process according to claim 7, wherein 0.5 to 1 molar equivalent of mineral acid is used.

9. A process according to claim 1 for the preparation of N-methyl-N,N-diallylamine, which comprises charging 1 molar equivalent of (para)formaldehyde and 1 molar equivalent of formic acid to a reactor in the presence of water, heating the reaction solution to a temperature of 40° to 100° C., and adding 1 molar equivalent of N,N-diallylamine while keeping the pH of the reaction mixture in the range of from 4–6 by addition of mineral acid until completion of the reaction.

* * * * *